(12) United States Patent
Fehrenbacher et al.

(10) Patent No.: US 6,558,794 B1
(45) Date of Patent: May 6, 2003

(54) CERAMIC PARTICULATE REINFORCED ORTHOPEDIC IMPLANTS

(75) Inventors: Larry Lee Fehrenbacher, Annapolis, MD (US); Mark Patterson, Annapolis, MD (US); Walter Zimbeck, Annapolis, MD (US)

(73) Assignee: Technology Assessment & Transfer, Inc., Annapolis, MD (US)

( * ) Notice: Subject to any disclaimer, the term of this patent is extended or adjusted under 35 U.S.C. 154(b) by 37 days.

(21) Appl. No.: 09/603,755

(22) Filed: Jun. 26, 2000

(51) Int. Cl.[7] .............................................. A61L 27/44
(52) U.S. Cl. .................... 428/402; 428/403; 428/404; 264/126; 524/404; 524/428; 524/430; 524/437; 623/16.11; 623/18.11
(58) Field of Search .................. 623/16.11, 18.11, 623/22.11, 23.56, 23.58; 524/428, 430, 437, 442, 438, 404; 428/403, 402, 404; 264/126

(56) References Cited

U.S. PATENT DOCUMENTS

| | | | | |
|---|---|---|---|---|
| 4,609,527 A | * | 9/1986 | Rinderle et al. ............. | 264/125 |
| 5,221,061 A | * | 6/1993 | Nishioka et al. ......... | 226/196.1 |
| 5,292,584 A | * | 3/1994 | Howard et al. ............. | 428/327 |
| 6,267,590 B1 | * | 7/2001 | Barry et al. .................. | 433/20 |

FOREIGN PATENT DOCUMENTS

EP          0 472 237 A1  *  2/1992

* cited by examiner

Primary Examiner—D. Lawrence Tarazano

(57) ABSTRACT

Material compositions for use in orthopedic implants comprising blends of ultra high molecular weight polyethylene (UHMWPE) and hard ceramic powders prepared by blending powdered UHMWPE and the ceramic powder in a high shear mixer are described. Orthopedic implants are then fabricated by pressure/thermo-forming the ceramic/polymer blend into a net shape prosthesis or a rod suitable for subsequently machining the desired components using diamond tooling. Net shape forming is the preferred method for preparing the orthopedic implants.

10 Claims, 1 Drawing Sheet

CERAMIC PARTICULATE REINFORCED ORTHOPEDIC IMPLANTS

FIELD OF THE INVENTION

The present invention relates to orthopedic implants and more specifically to consolidated ceramic reinforced polymers useful in orthopedic implant applications.

BACKGROUND OF THE INVENTION

For at least three decades, ultra high molecular weight polyethylene (UHMWPE) has dominated the joint replacement arena as the material of choice in joint prostheses, i.e. primarily hip and knee replacements.

The principle limitation controlling the longevity of hip prostheses is the body's reaction to UHMWPE debris generated during interaction with the articulating femoral ball. The UHMWPE debris has been linked to bone resorption (osteolysis) which leads to loosening and premature failure of the implant.

Failure of total knee replacements is largely associated with high stress fatigue loads that result in pitting, crack propagation and delamination of UHMWPE in such applications. For example, normal activities such as walking and climbing stairs can impose forces between the tibia and femur that are approximately four to five times ones body weight. Recent studies have shown that out of 937 tibial bi-compartmental and uni-compartmental bearings, 50% had indications of delaminations and cracking. In fact, total joint implants rarely last over ten years today. The rapidly growing aging population and the increasing use of implants in younger people provides a strong mandate for longevity improvements in total joint arthroplasties. Thus, numerous approaches to improving the useful life of such devices have been and continue to be proposed.

Among the proposed improvements are; advanced crosslinking methods, carbon fiber reinforcement, and the use of a variety of counterface materials including CoCr, Ti-6Al-4V, and ceramics. Quite recently, surface engineering of metal counterfaces, e.g. coating, implantation, oxidation and diffusion has also been evaluated for reducing the wear rate of the preferred UHMWPE materials.

Currently, most standard polyethylene components are irradiated with 5 Mrad of gamma radiation in a nitrogen atmosphere and the heated to 155° C. for 24 hours to remove free radicals before being machined into components. Considerable research has been and continues to be expended to reduce wear rates and creep in UHMWPE since none of the foregoing methods has supplied a satisfactory solution.

A method that uses high pressure to produce a more highly crystallized polyethylene (PE) (80% compared to 55% for normal irradiated PE) produced a material that exhibited higher yield stress, modulus and resistance to creep and crack growth, but neither laboratory wear tests nor clinical trials have demonstrated improvement in wear resistance.

Numerous efforts have attempted to improve the performance of UHMWPE by increasing the cross-linking to improve its wear resistance. These efforts have included the application of higher doses of gamma radiation, electron beam radiation, and heating in combination with irradiation and chemical peroxide treatments to increase the degree of cross-linking.

The mechanical properties of enhanced cross-linked PEs show a decrease in yield stress, elastic modulus, tensile strength, creep resistance, toughness and elongation to failure accompanied by an improvement in wear resistance. Since strength and creep resistance are crucial to extending the life of prostheses it is essential that these properties not be negatively impacted as other properties such as wear resistance are enhanced.

Alternative materials have also been used to approach the solution to the prosthesis wear problem. Several different polymeric materials have, for example, been evaluated over the years. Polytetrafluoroethylene, various polyesters and polyacetyls have been evaluated without finding a successful replacement for UHMWPE.

Chopped carbon fiber reinforced PE while demonstrating promising results in bench scale screening and simulator tests failed in clinical trials. Chopped carbon fiber reinforced epoxy-based cups articulating against alumina heads have demonstrated five times lower wear rates than UHMWPE cups in early clinical trials.

In summary, although a large number of solutions have been proposed to provide improved hip and knee replacement materials, UHMWPE remains the current, if not entirely satisfactory, material of choice in such applications and the provision of an improved material or combination of materials which would provide improved wear resistance and strength for such uses remains an elusive objective.

OBJECTS OF THE INVENTION

It is therefore an object of the present invention to provide an improved material for use in orthopedic implants.

It is another object of the present invention to provide such an improved material that exhibits enhanced wear resistance and strength over existing and currently used UHMWPE materials.

It is yet a further object of the present invention to provide improved orthopedic implants that exhibit useful lives beyond those implants currently in use today.

SUMMARY OF THE INVENTION

Figure 1:
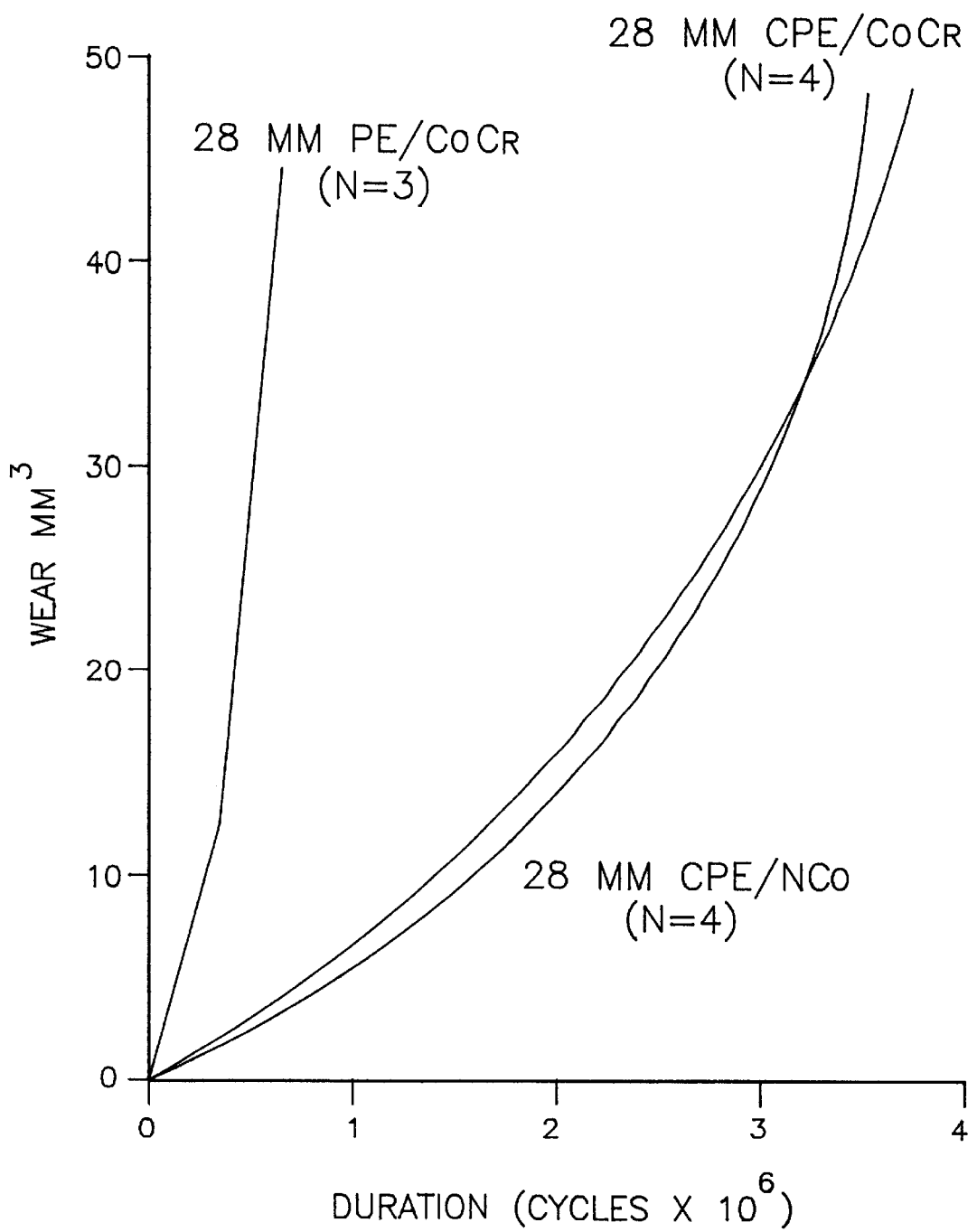
FIG. 1 shows a graph representing the relative wear rates of various implant materials as compared to those of the instant invention.

The present invention describes improved material compositions for use in orthopedic implants comprising blends of UHMWPE and hard ceramic powders prepared by blending powdered UHMWPE and the ceramic powder in a high shear mixer. Orthopedic implants are then fabricated by pressure/thermo-forming the ceramic/polymer blend into a net shape prosthesis or a rod or other shape suitable for subsequently machining the desired components using diamond tooling. Net shape forming is the preferred method for preparing the orthopedic implant.

DETAILED DESCRIPTION

The improved prosthetic materials of the present invention comprise intimate blends of UHMWPE powder and hard ceramic powders formed by blending in a high shear mixer that are subsequently thermo-formed, under pressure, i.e. compression molded, into either net shape prosthetics or rods or the like that can be further fabricated by machining to obtain the required prosthetic shape.

UHMWPE suitable for use in the materials and devices of the present invention include those having a molecular weight above about 3,000,000 UHMWPE materials having a molecular weight between about 4,000,000 and about 6,000,000 are specifically preferred. For the blending process, UHMWPE powders having particle sizes ranging from about 75 $\mu$m to about 150 $\mu$m are generally satisfactory for use in the preparation of the materials of the present invention.

The hard ceramic powders suitable for use in the compositions and devices described herein include, but are not limited to, such materials as boron carbide, aluminum oxide, silicon carbide, titanium carbide, titanium diboride, and the like that exhibit high wear resistance properties and a general physiological inertness in anatomical applications. In order to achieve appropriate blending of the UHMWPE and the ceramic powder, it is preferred that the particle size of the ceramic powder be between about 0.1 $\mu$m and about 100 $\mu$m with an average particle size of from about 0.3 $\mu$m to about 75 $\mu$m. According to a highly preferred embodiment, ceramic particles on the order of between about 0.3 $\mu$m and about 20 $\mu$m are used to prepare the materials of the present invention.

The powder blends of the present invention comprise from about 0.5 to about 10 volume percent of the ceramic powder in the UHMWPE. Preferably, a volume percent of from about 1 volume percent to about 5 volume percent ceramic powder in UHMWPE is used. According to a highly preferred embodiment of the present invention, a concentration of from about 1 volume percent to about 2 volume percent ceramic powder in UHMWPE is used.

Preparation of the ceramic/polymer blends of the present invention is accomplished by blending the above-described components in the indicated ratios in high shear blending equipment of the type described below for a period of more than about 10 minutes and preferably for from about 15 to about 20 minutes at room temperature.

Blending of the UHMWPE powder and the hard ceramic powder is preferably performed in a high shear blending apparatus; ball mills that provide such a high shear level have been found suitable for this application. Other useful such high shear mixers include ribbon blenders and the like.

The ceramic/polymer powder blends of the present invention prepared as just described are then formed into orthopedic implants by thermo-forming under pressure, in for example a compression molding press, into net shape prostheses or thermo-forming under pressure into rods or other shapes suitable for subsequent machining into implants. Thermo-forming is accomplished by placing the powder blend into a press and preheating at a temperature at or above about 190° C. in an inert atmosphere such as nitrogen or argon for a period of from about 30 minutes to about two or more hours in order to remove residual oxygen and/or moisture. The temperature of the molding press is then raised to a temperature of about 220° C., preferably between about 210 and about 225° C. and pressure applied at between about 500 and about 2000 psi, preferably between about 800 psi and about 1200 psi for a period of from about 15 minutes to about 2 hours. Controlled cooling to ambient temperature or about 40° C. is performed while maintaining the press under pressure. Cooling is preferably carried out at a rate of between about 2° C. and about 3° C./minute. Upon attaining about 40° C. the pressure is released.

The foregoing describes the basic blending and implant preparation compositions and procedures. A variety of supplemental or additional modifications/procedures that may be performed upon either the polymer/ceramic powder blend and/or the shaped implant or precursor that further enhance the properties of the implant product will now be described.

The wear resistance of a net shape implant prepared in a press or machined as just described can be further improved by the application of a wear resistant surface to the wearing surfaces of the implant. For example, a wear surface of about 100 alternating layers of $B_4C$ and Mo each about 50 angstroms thick in the femur head area of the net shapes in accordance with the procedure described hereinafter can be applied as may other wear resistance enhancing coatings and treatments.

The preferred method for applying such coatings is magnetron sputtering. The alternating layers are produced by rotating the femur ball as it is translated in front of $B_4C$ and Mo targets. Sputtering parameters for $B_4C$ are in the range of 750 W to 2000 W target power either RF or DC and between 300 W and 600 W DC for the Mo target. The preferred power is 800 W RF for $B_4C$ and 400 W DC for Mo. Chamber pressures of about 2.5 millitore argon are preferred. Devices treated in this fashion were subsequently evaluated in a hip simulator at Loma Linda University against similarly coated and uncoated 28 mm femoral heads using bovine serum as a lubricant. The results of such testing are presented in FIG. 1 and show that the wear rate for the ceramic filled UHMWPE cups (curve A) prepared in accordance with the present invention is about three times less than that of the unfilled system (curve B) that was simultaneously evaluated. The ceramic filled UHMWPE against coated CoCr (CPE/NCo in FIG. 1) showed 68% less wear than the control and 12% less wear than the ceramic-filled UHMWPE uncoated CoCr combination (CPE/CoCr in FIG. 1) after 4 million cycles in a hip simulator.

Since coupling agents are conventionally used to achieve chemical bonding, and therefore better mechanical properties, between inorganic ceramics and organic matrices, it is also possible in the instant blended powder compositions to utilize similar procedures. For example, the ceramic powder, $Al_2O_3$ having a particle size <0.3 $\mu$m can be ball milled for several hours with a dilute solution such as 5 weight percent silane coupling agent, specifically gamma-methacryloxypropyl trimethoxysilane (gamma-MTS) in isopropyl alcohol. Coupling agents of this type contain an anchor group that reacts with absorbed OH groups on the surface of the inorganic powder forming a chemically bonded monolayer. The other end of the coupling agent is a long chain polymer selected to be compatible with the matrix polymer. A "coupled" ceramic/polymer powder is prepared by drying the ceramic powder after ball milling, and then blending as described above with from about 0.75 to about 5 volume % treated ceramic powder in UHMWPE in a high shear mixer as described above. The blended mixture is then warm pressed at a temperature of about 190° C. for about one hour under a nitrogen or other inert atmosphere to remove residual oxygen/moisture. The blend is then pressed at a temperature approaching the melting point of the polymer, about 220° C. and held under at least 500 psi pressure for a period of about 30 minutes to about two hours. While pressure is maintained, the press is cooled at a rate of about three degrees/minute to a temperature of about 40° C., the pressure released and the part removed from the press as a net shape implant or a shape suitable for machining into an appropriate implant.

Since it has been previously demonstrated in the prior art that "as formed" surfaces contribute to lower wear rates than machined surfaces, it is preferred in the successful practice of the instant invention that net shape implants be fabricated from the ceramic/polymer powder blends described.

As the invention has been described, it will be apparent to those skilled in the art that the same can be varied in many ways without departing from the spirit and scope of the invention. Any and all such modifications are intended to be included within the scope of the appended claims.

What is claimed is:

1. A thermo-processable material for use in the fabrication of orthopedic implants comprising a hard ceramic powder having a particle size between about 0.1 μm and about 100 μm and an average particle size between about 0.3 μm and about 20 μm coupled to polyethylene having a molecular weight of between about 3,000,000 and about 6,000,000 via a coupling agent comprising an anchor group that reacts with hydroxyl groups absorbed by said hard ceramic powder and a long chain polymer compatible with said polyethylene.

2. The thermo-processable material of claim 1 wherein said coupling agent is a silane coupling agent.

3. The thermo-processable material of claim 2 wherein said silane coupling agent comprises gamma-methacryloxypropyl trimethoxysilane (gamma-MTS) in isopropyl alcohol.

4. The thermo-processable material of claim 1 wherein said hard ceramic powder comprises from about 0.5 volume percent to about 10 volume percent of said melt-processable material.

5. The thermo-processable material of claim 1 wherein said hard ceramic powder is selected from the group consisting of hard ceramic nitrides, carbides, borides and oxides.

6. An orthopedic implant comprising a compression molded shape of a thermo-processable material for use in the fabrication of orthopedic implants comprising a hard ceramic powder having a particle size between about 0.1 μm and about 100 μm and an average particle size between about 0.3 μm and about 20 μm coupled to polyethylene having a molecular weight of between about 3,000,000 and about 6,000,000 via a coupling agent comprising an anchor group that reacts with hydroxyl groups absorbed by said hard ceramic powder and a long chain polymer compatible with said polyethylene.

7. The orthopedic implant of claim 6 wherein said coupling agent is a silane coupling agent.

8. The orthopedic implant of claim 7 wherein said silane coupling agent comprises gamma-methacryloxypropyl trimethoxysilane (gamma-MTS) in isopropyl alcohol.

9. The orthopedic implant of claim 6 wherein said hard ceramic powder comprises from about 0.5 volume percent to about 10 volume percent of said melt-processable material.

10. The orthopedic implant of claim 6 wherein said hard ceramic powder is selected from the group consisting of hard ceramic nitrides, carbides, borides and oxides.

* * * * *